United States Patent [19]

McCaman et al.

[11] Patent Number: 5,176,910
[45] Date of Patent: Jan. 5, 1993

[54] TREPONEMA HYODYSENTERIAE HEMOLYSIN AND USES THEREFOR

[75] Inventors: Michael McCaman, San Bruno; Raymond Slomiany, Emeryville, both of Calif.

[73] Assignee: ML Technology Ventures, L. P., New York, N.Y.

[21] Appl. No.: 296,958

[22] Filed: Jan. 17, 1989

[51] Int. Cl.⁵ .................... A61K 39/02; C07K 3/00
[52] U.S. Cl. ................................ 424/92; 424/88; 530/350
[58] Field of Search .................. 424/88, 92; 530/350

[56] References Cited

FOREIGN PATENT DOCUMENTS 0282965 9/1988 European Pat. Off. .

OTHER PUBLICATIONS

Knoop, *Infection and Immunity*, vol. 31, No. 1, pp. 193-198 (1981).
Sahib et al., *Current Microbiology*, vol. 5, pp. 91-94, 1981.
Leincke et al., *Journal of Medical Microbiology*, vol. 15, pp. 205-214 (1982).
Kinyon et al., *Int. J. Sys. Bacteriol.*, vol. 29, pp. 102-109, Apr. 1979.
Saheb et al., *Biochemie*, vol. 62, pp. 779-785, 1980.
Kent et al., *J. Med. Microbiol.*, vol. 27, pp. 215-224, 1988.

*Primary Examiner*—Johnnie R. Brown
*Assistant Examiner*—Abdel A. Mohamed
*Attorney, Agent, or Firm*—Elliott M. Olstein; Raymond J. Lillie

[57] ABSTRACT

A vaccine for protection against swine dysentery which comprises *T. hyodysenteriae* hemolysin and a physiologically acceptable vehicle for said peptide. The vaccine contains the hemolysin in an amount effective for protecting against swine dysentery. The invention also relates to a method of protecting swine against swine dysentery by administering to swine the vaccine described above.

16 Claims, No Drawings

TREPONEMA HYODYSENTERIAE HEMOLYSIN AND USES THEREFOR

This invention relates to *Treponema hyodysenteriae* (*T. hyo.*), and more particularly to hemolysin, or hemolytic factor, produced by *Treponema hyodysenteriae*. Still more particularly, the invention relates to a vaccine for swine dysentery.

Swine dysentery is a severe infectious disease found in all major pig-rearing countries. The symptoms of swine dysentery are severe mucohemorrhagic diarrhea, dehydration, and weight loss.

It has been discovered that swine dysentery is caused by *Treponema hyodysenteriae*, an anaerobic, B-hemolytic spirochete. To date, no one has demonstrated virulence in non-hemolytic strains of *Treponema hyodysenteriae*.

The disease generally results from ingestion of feces containing *T. hyodysenteriae* from actuely infected or asymptomatic carrier pigs or by feces spread by farm equipment or handlers.

There have been previous attempts to provide a vaccine against *Treponema hyodysenteriae* which have generally involved use of the whole organism.

In accordance with one aspect of the present invention, there is provided a vaccine and a method for protection against swine dysentery. The vaccine comprises a hemolysin (hemolytic factor). The vaccine is free from *T. hyodysenteriae* cells and contains the hemolysin in an amount effective for protecting against swine dysentery. The method for protecting swine against swine dysentery comprises administering to swine *T. hyodysenteriae* hemolysin in an amount effective to protect against swine dysentery.

The hemolysin to be used in the vaccine may be isolated from *T. hyodysenteriae* by culture methods and other means known in the art. For example, hemolysin can be produced by culturing *T. hyodysenteriae* cells on a blood agar medium or by culturing *T. hyodysenteriae* cells in culture broth. The hemolysin is then separated from the cells. The hemolysin is then treated with acid pH, ammonium sulfate salts, and then the hemolysin is separated from the mixture by ion-exchange chromatography and/or gel filtration.

In culturing *T. hyodysenteriae* cells for the preparation of the hemolysin, the hemolysin, may be induced by adding RNA such as yeast RNA, Na-RNA, $Mg^{2+}$-RNA and tRNA molecules which have been partially cleaved by ribonuclease, to the *T. hyodysenteriae* culture. After induction of the RNA, the *T. hyodysenteriae* cells are separated from the rest of a culture broth preparation by means such as centrifugation. The supernatant is then treated by means such as described above in order to obtain purified hemolysin. Recombinant methods may also be employed for producing *T. hyo.* hemolysin to be used in a vaccine.

The *T. hyo.* hemolysin in conjunction with a physiologically acceptable carrier, is employed as a vaccine to provide protection against swine dysentery and in particular swine dysentery induced by *T. hyodysenteriae*. The *T. hyo.* hemolysin is employed in the vaccine in an amount effective to provide protection against swine dysentery. The hemolysin may be administered in an amount of from about 25,000 to about 1,000,000 units per dose, preferably from about 100,000 units to about 500,000 units per dose. Hemolysin units may be determined through an assay procedure disclosed in an article by Knoop in *Infection and Immunity*, Volume 31, No. 1, pgs. 193–198 (1981).

The term "protection" or "protecting" when used with respect to the vaccine for swine dysentery described herein means that the vaccine prevents swine dysentery and/or reduces the severity of swine dysentery.

In one embodiment, the vaccine is prepared by admixing the *T. hyo.* hemolysin with an adjuvant such as mineral oil, although other adjuvants may also be used, such as alum and synthetic polymers. Carriers for vaccines are well-known in the art and the selection of a suitable carrier is deemed to be within the scope of those skilled in the art from the teachings herein. The selection of a suitable carrier is also dependent upon the manner in which the vaccine is to be administered. The vaccine may be in the form of an injectable dose and may be administered intra-muscularly, intravenously, or by sub-cutaneous administration. It is also possible to administer the vaccine orally by mixing the active components with feed or water or by providing a tablet form, etc.

Other means for administering the vaccine should be apparent to those skilled in the art from the teachings herein; accordingly, the scope of the invention is not limited to a particular delivery form.

In another embodiment of the present invention, the *T hyo.* hemolysin may be employed in a vaccine in conjunction with one or more proteins which are capable of eliciting antibodies which recognize a *T. hyo.* antigen having a molecular weight of from about 19 kda to about 90 kda, and preferably such *T. hyo.* antigen which is recognized has a molecular weight of at least 25 kda and most generally the molecular weight does not exceed 65 kda. In a particularly preferred embodiment such protein or proteins elicit an antibody which recognizes one or more of the *T. hyo.* antigens having the following molecular weights: 19 kda; 29 kda; 30 kda; 31 kda; 34 kda; 36 kda; 38 kda; 39 kda; 42 kda; 44 kda; and 60 kda. In general, such protein or proteins will immunoreact with serum of swine convalescing from swine dystentery. Such protein may be the corresponding *T. hyo.* antigen and/or a fragment and/or derivative thereof. Such protein or proteins, as may be used in combination with *T. hyo.* hemolysin in a physiologically acceptable vehicle as a vaccine for protecting swine against swine dysentery.

The *T. hyodysenteriae* antigen(s) and/or fragment(s) and/or derivative(s) thereof, when used in conjunction with *T. hyodysenteriae* hemolysin in a vaccine, is employed in said vaccine in an amount of at least 5 micrograms per dose, and preferably in an amount of at least 100 micrograms per dose. In most cases, the vaccine does not include such antigen(s) and/or fragment(s), and/or derivative(s) thereof in an amount greater than 20 milligrams.

The molecular weights for characterizing the antigen(s) are obtained by discontinuous polyacrylamide gel electrophoresis using the SDS buffer system described by Laemmli *Nature* 227; 680–85 (London 1970) with an acrylamide concentration of 10–17% and a bis-acrylamide to acrylamide ratio of 1:29.

Particularly preferred are proteins which elicit antibodies which recognize a *T. hyo.* antigen having a molecular weight of about 38 kda, 39 kda, 42 kda, or 60 kda; in particular 42 kda. There may be more than one *T. hyo.* protein or antigen having each of such molecular weights.

The *T. hyo.* proteins used in combination with the hemolysin may be obtained as described in U.S. application Ser. No. 026,781 or Ser. No. 165,305, both now abandoned.

Alternatively, the protein or proteins capable of eliciting an antibody which recognizes the noted *T. hyo.* antigen or antigens, which are used in combination with *T. hyo.* hemolysin may be obtained by recombinant techniques, for example, as described in U.S. application Ser. No. 213,262 filed on Jun. 29, 1988, which is hereby incorporated by reference.

In another embodiment, the *T. hyo.* hemolysin, is partially inactivated by cross-linking the hemolysin to a carrier peptide such as a lysozyme in order to try to heighten the immune responses to the hemolysin. The lysoszyme may be in an active or an inactive form.

Although both of the above embodiments of the vaccine are effective in reducing the weight loss of pigs orally challenged and infected with *T. hyodysenteriae*, the scope of the invention is not intended to be limited to these embodiments of the vaccine.

The *T. hyodysenteriae* hemolysin which may be employed in a preferred embodiment of the vaccine of the present invention is of a structure which appears not to be related to hemolysins produced by other microorganisms. Most hemolysins produced by other bacteria are large peptide molecules having a molecular weight from about 30,000 to about 70,000. The *T. hyodysenteriae* hemolysin is not related to these hemolysins, but instead appears to be a close analog of streptolysin S, which is produced by a gram positive Streptococcus. The streptolysin S molecule has been characterized as a small peptide of about 30 amino acids, but has not proven to be such a peptide nor has its gene been cloned.

The *T. hyodysenteriae* hemolysin has been shown to act like an enterotoxin when applied to isolated swine mucosal tissue. The hemolysin has also been shown to be cytopathic, or cytotoxic, to Chinese hamster ovary cells, Bowes melanoma cells, and red blood cells.

The following Examples will demonstrate the preparation of *T. hyo.* hemolysin and the effectiveness of an embodiment of a vaccine in accordance with the present invention.

EXAMPLE 1

Method of Preparation of T. Hyo Hemolysin

The isolation and initial characterization of hemolysin produced by *T. hyo.* has been described in the literature (Knoop, 1981; Saheb, et al., *Current Mirobiology*, Vol. 5 pgs. 91-94 (1981); and Lemcke, et al., *Journal of Medical Microbiology*, Vol. 15 pgs. 205-214 (1982). In laboratory culture this hemolysin can be obtained in highest yield by adding an inducer to actively growing cells. The best inducer to date is a fraction of yeast RNA obtained by exhaustive digestion of total RNA with ribonuclease A. The residual large Molecular Weight RNA, called RNA core, was obtained from Sigma Chemical, a stock solution of 100 mg/ml was made in water and then filter sterilized and stored frozen. RNA core was added to a final concentration of 0.5 mg/ml in an anaerobic culture of *T. hyo.* strain B204 or B234 with an optical density (A600) of about 0.1. Cells were grown for 4-8 hours in the presence of inducer and then the culture was harvested by centrifugation. Hemolysin is found only in the cell free culture supernatant and is first concentrated by acidification of the culture broth to a pH of 3.0 by addition of 5N HCl. The resulting cloudy solution is then stirred and centrifuged 10 min. @ $10,000 \times g$. The pellet fraction (containing the hemolysin activity) is solubilized by resuspension in 1/20 the starting volume of 25 mM $NaPO_4$ buffer pH 7. This solution is usually turbid because the pH drops as the hemolysin precipitate solubilizes and requires the addition of $Na_2HPO_4$ until the final pH rises to 6.0. At this point, 43 gms of ammonium sulfate crystals is added to 100 mls of solution (65% saturation), stirred for 2 hours at 4° C. and centrifuged at $10,000 \times g$ for 10 min. The supernatant fraction containing the hemolysin, is dialyzed extensively against 10 mM $NaPO_{(4)}$, pH 6.5. Sodium chloride is added to this solution to reach 200 mM, then it is loaded onto a column of DEAE Sephacel (Pharmacia) equilibrated in the same buffer. The DEAE bound sample is washed with 4 column volumes of 200 mM NaCl, phosphate buffer and then eluted with 750 mM NaCl in the same phosphate buffer. Hemolysin activity is co-eluted with a large peak of RNA detectable by brown color as well as high A260. This hemolysin-RNA material appeared to be free of all protein $\geq 15,000$ M.W. as judged by SDS-PAGE. The hemolysin was dialyzed against 10 mM ammonium bicarbonate pH 6.8, then lyophilized, reconstituted in a small volume of water and stored frozen at $-20°$ C. Quantitation of hemolysin activity was done by a standard assay of lysis of washed red blood cells. (Knoop, et al.)

EXAMPLE 2

Use of Hemolysin as a Vaccine

The hemolysin (2 mls, 125,000 units/ml) was mixed with a mineral oil adjuvant (0.5 ml) and administered intramuscularly to 30-40 lb piglets twice over an 8 week period. Animals were then orally inoculated with strain B204 ($10^9$ cells over a 2 day period) and then monitored for signs of swine dysentery. Weight measurements were also made up to 35 days after the oral challenge. The control animals received no injection. The experimental results are shown below.

| No. pigs | Onset days (avg.) | Diarrhea score (avg.) | Blood score (avg.) | General Health (avg.) | Weight gain day 0-35, % |
|---|---|---|---|---|---|
| Controls 5 | 13 | 14 | 10 | 2 | 25 |
| Vaccinates 5 | 19 | 11 | 8 | 0 | 49 |

Scores indicate number of days pigs showed a grade of 3 or 4 for each category.

Grading is as follows:

Diarrhea:
1. Solid normal
2. Soft
3. Very soft to loose
4. Very loose, watery

Blood:
1. Normal
2. Slight amount of mucus.
3. Large amount of mucus flecks of blood
4. Extremely bloody.

General Health

1. Normal, alert.
2. Slightly gaunt, slightly rough hair coat.
3. Very gaunt, very rough hair, dull eyes.
4. Moribund.

The above example shows that the symptoms and effects of swine dysentery were alleviated in those pigs which received a vaccine of the present invention prior to the oral challenge.

EXAMPLE 3

Use of Hemolysin in a Combination Vaccine

In a follow-up study hemolysin was tested alone and in combination with a purified T. hyo antigen. Purification of the 42 kDa antigen is disclosed in the co-pending patent application U.S. Ser. No. 165,305.

Six pigs per test group were used. The pigs averaged 22.6 lb and were approximately 5-6 weeks of age. Five groups of pigs were given two doses, the first on day 0 and a booster on day 36. The injections were given I.M., in the neck with at 1 mg/dose of 42 kDa native antigen and/or 250,000 units/dose of hemolysin. Animals were challenged on day 50 injection by stomach intubation using a pure culture of T. hyo at $5.5 \times 10^2$ cfu per pig. The study was terminated on day 92.

Vaccines were given with Emulsigen adjuvant. Emulsigen was used as an adjuvant control, mixed with Dulbeco's PBS buffer.

Animals were monitored daily for clinical signs of swine dysentery. Microbiological evaluation of routine weekly rectal swabs was conducted for T. hyo and Salmonella. Animals showing signs of bloody diarrhea were swabbed and evaluated on that day. Weekly post-challenge, pigs were weighed and their feed intake determined. The experimental results are shown below.

Although in this study, vaccination with hemolysin did not protect the animals better than adjuvant alone the combination of hemolysin plus 42 kDa indicates that there may be a synergistic effect when the hemolysin is used in a combination treatment.

It is to be understood, however, that the scope of the present invention is not to be limited to the specific embodiments described above. The invention may be practiced other than as particularly described and still be within the scope of the accompanying claims.

What is claimed is:

1. A vaccine for protection against swine dysentery, comprising:
   T. hyodysenteriae hemolysin, and a physiologically acceptable carrier, said vaccine being essentially free of T. hyodysenteriae cells and further comprising said hemolysin in an amount effective for protecting against swine dysentery.

2. The vaccine of claim 1, and further comprising:
   at least one protein which elicits antibodies which recognize a T. hyodysenteriae antigen having a molecular weight of from about 19 kda to about 90 kda.

3. The vaccine of claim 2 wherein said at least one protein elicits an antibody which recognizes at least one of the 19 kda, 29 kda, 30 kda, 31 kda, 34 kda, 36 kda, 38 kda, 39 kda, 42 kda, 44 kda, and 60 kda T. hyodysenteriae antigens.

4. The vaccine of claim 3 wherein said at least one protein elicits an antibody which recognizes at least one of the 38 kda, 39 kda, 42 kda, and 60 kda T. hyodysenteriae antigens.

5. The vaccine of claim 4 wherein said at least one protein elicits an antibody which recognizes the 42 kda antigen.

6. A method for protecting swine against swine dysentery, comprising:
   administering to swine T. hyodysenteriae hemolysin, and a physiologically acceptable carrier, said hemolysin being administered in an amount effective to protect against swine dysentery.

7. A method for protecting swine against swine dysentery, comprising
   administering to swine a vaccine comprising T. hyodysenteriae hemolysin and at least one protein which elicits antibodies which recognize a T. hyodysenteriae antigen having a molecular weight of from about 19 kda to about 90 kda, and a physiologically acceptable carrier, said hemolysin and said at least one protein being administered in amounts effective to protect swine against swine dysentery.

8. The method of claim 7 wherein said at least one protein elicits an antibody which recognizes at least one of the 19 kda, 29 kda, 30 kda, 31 kda, 34 kda, 36 kda, 38 kda, 39 kda, 42 kda, and 60 kda T. hyodysenteriae antigens.

9. The method of claim 8 wherein said at least one protein elicits an antibody which recognizes at least one of the 38 kda, 39 kda, 42 kda, and 60 kda T. hyodysenteriae antigens.

10. The method of claim 9 wherein said at least one protein elicits an antibody which recognizes the 42 kda T. hyodysenteriae antigen.

11. The method of claim 6 wherein said hemolsyin is administered in an amount of from about 25,000 units to about 1,000,000 units per dose.

12. The method of claim 11 wherein said hemolysin is administered in an amount of from about 100,000 units to about 500,000 units per dose.

13. The method of claim 7 wherein said hemolysin is administered in an amount of from about 25,000 units to about 1,000,000 units per dose.

14. The method of claim 13 wherein said hemolysin is administered in an amount of from about 100,000 units to about 500,000 units per dose.

15. The method of claim 7 wherein said T. hyodysenteriae antigen(s) or fragment(s), or derivative(s) thereof is administered in an amount of at least 5 micrograms per dose.

16. The method of claim 15 wherein said T. hyodysenteriae antigen(s) or fragment(s) or derivative(s) thereof is administered in an amount of at least 100 micrograms per dose.

* * * * *